United States Patent [19]

Bowden

[11] Patent Number: 5,392,952
[45] Date of Patent: Feb. 28, 1995

[54] PILL DISPENSISNG DEVICE PROVIDING OVERDOSAGE PROTECTION

[76] Inventor: James R. Bowden, 11 Maple Rock Rd., N. Scituate, R.I. 02857

[21] Appl. No.: 179,523

[22] Filed: Jan. 10, 1994

[51] Int. Cl.⁶ .............................................. B65B 59/00
[52] U.S. Cl. .................................... 221/15; 221/3; 221/76
[58] Field of Search .................... 221/2, 3, 7, 9, 15, 221/97, 99, 100, 191, 82, 76, 79

[56] References Cited

U.S. PATENT DOCUMENTS

| | | | |
|---|---|---|---|
| 3,369,697 | 2/1968 | Glucksman et al. | 22/19 |
| 3,722,739 | 3/1973 | Blumberg | 221/3 |
| 3,762,601 | 10/1973 | McLaughlin | 221/154 |
| 3,964,638 | 6/1976 | Dimauro | 221/3 |
| 3,968,900 | 7/1976 | Stambuk | 221/3 |
| 4,223,801 | 9/1980 | Carlson | 221/3 |
| 4,310,103 | 1/1982 | Reilly, Jr. et al. | 221/15 |
| 4,526,474 | 7/1985 | Simon | 368/10 |
| 4,572,403 | 2/1986 | Benaroya | 221/3 |
| 4,626,105 | 12/1986 | Miller | 368/10 |
| 4,660,991 | 4/1987 | Simon | 368/10 |
| 4,662,537 | 5/1987 | Wolf et al. | 221/89 |
| 4,674,652 | 6/1987 | Aten et al. | 221/3 |
| 4,695,954 | 9/1987 | Rose et al. | 364/413 |
| 4,717,042 | 1/1988 | McLaughlin | 221/3 |
| 4,725,997 | 2/1988 | Urquhart et al. | 368/10 |
| 4,731,765 | 3/1988 | Cole et al. | 368/10 |
| 4,747,514 | 5/1988 | Stone | 221/4 |
| 4,763,810 | 8/1988 | Christiansen | 221/3 |
| 4,768,177 | 8/1988 | Kehr et al. | 368/10 |
| 4,807,757 | 2/1989 | Rappaport et al. | 206/535 |
| 4,815,606 | 3/1989 | Airola | 206/532 |
| 4,872,591 | 10/1989 | Konopka | 221/3 |
| 4,889,238 | 12/1989 | Batchelor | 206/535 |
| 4,905,866 | 3/1990 | Bartell et al. | 221/5 |
| 4,953,745 | 9/1990 | Rowlett, Jr. | 221/5 |
| 5,170,380 | 12/1992 | Howard et al. | 221/15 |
| 5,200,891 | 4/1993 | Kehr et al. | 221/15 |
| 5,291,191 | 3/1994 | Moore | 221/3 |

Primary Examiner—Kenneth W. Noland
Attorney, Agent, or Firm—Samuels, Gauthier & Stevens

[57] ABSTRACT

A medication dispensing device for providing medication doses within selected periods of time. The device comprises a housing unit defining a first and second opening, a medication containment unit, a request signal generating unit, a dispensing unit, a medication collection unit, and a control unit. The medication containment unit includes a plurality of sealed dosage compartments received within the first opening in the housing. Each of the dosage compartments has an associated time period during which the dosages may be dispensed. The request signal generating unit generates a request signal. The dispensing unit causes medication doses that are requested within their respective time periods to be dispensed from the device through the second opening. The medication collection unit prevents medication doses that are not requested within their respective time periods from being dispensed from the device. The control unit controls the dispensing unit and the medication collection unit, responsive to the request signal and the time periods.

9 Claims, 12 Drawing Sheets

PILL DISPENSISNG DEVICE PROVIDING OVERDOSAGE PROTECTION

BACKGROUND OF THE INVENTION

The invention relates generally to systems for, and methods of, automatically dispensing medication in a home setting in accordance with a predetermined schedule, and relates specifically to systems which are both easy to use by elderly or disabled people yet provide protection against underdosage as well as overdosage.

Underdosage protection relates to a device's ability to alert a patient of the proper time to take medication. Overdosage protection relates to the ability of a pill device to prevent a user from taking more than one medication dose in a relatively short period of time. For example, overdosage could occur if a patient misses taking a medication on time and takes the missed medication immediately prior to the next dosage period. Overdosage would occur if the patient is permitted access to and takes both the untaken dose as well as the next dose soon thereafter.

Non-compliance with self-administered medication schedules is a costly health care problem. Approximately one third (11 million) of the non-institutionalized elderly experience at least some minor confusion sufficient to interfere with their normal activities of daily living, such as the taking of medication on a prescribed schedule. As the health care industry changes within the next several years, the importance of avoiding complications by employing preventive procedures such as the use of intelligent pill dispensers for home use will likely increase. Present pill devices, however are not well suited for such demanding applications.

Present pill providing devices include (1) reference aids for referencing when to take medication, (2) controlled access devices for limiting pill access to predefined periods of time, and (3) controlled medication dispensing devices which eject medication at predetermined times. Devices of category (1) are passive reference aids which do not prevent access to medication.

Devices of category (2), such as those disclosed in U.S. Pat. Nos. 4,725,997; 4,695,954; 4,572,403; 4,310,103; 4,223,801; 3,762,601; and 3,722,739, generally require that a user reach into the device to retrieve the medication at certain periods of time. Unfortunately such devices are difficult for individuals having low manual dexterity skills to use due to the requirement that a patient reach into an exposed recess.

Devices of category (3), such as those disclosed in U.S. Pat. Nos. 4,953,745; 4,872,591; 4,763,810; 4,747,514; 4,674,652; and 3,964,638, generally dispense or eject medication automatically on a timed sequence. These devices, however, do not adequately provide protection against overdosage in the situation when medication is not timely taken. Because such devices eject medication automatically, overdosage may occur.

Additional devices of category (3) include those disclosed in U.S. Pat. Nos. 3,968,900 and 3,368,967. These devices generally dispense or eject medication following a request by a user in cooperation with a timer. Although the dispensing mechanisms turn off their respective timers such that a predetermined period of time must elapse between dispenses, all of the medication doses for such devices must be the same since it is not known when specific doses will be taken. This may lead to adverse drug reactions if, for example, certain medication which should not be taken with food is taken at meal time because earlier medications were not taken on time. Also, no record is kept of the scheduling deviations that may occur with such an altered timing schedule.

Additionally, present devices are not sufficiently flexible in their ability to respond to various conditions involving interruptions in the dispensing schedule. A medication dispenser should be able to respond to interruptions by readjusting the schedule if necessary, or by preventing certain medication from being made available if requested too late.

Interruptions in a schedule can occur if medication is taken early, taken late, or not taken at all for a certain dosage period. The determination of how to adjust one's medication schedule once an interruption has occurred, is a difficult decision for many people. Questions whether the schedule should be shifted forward in time, whether the patient should skip the last dose, whether the patient should take both doses, or whether the patient should skip the next dose, are not always easily answered. Such answers regarding the most appropriate course of action depend upon the medication involved as well as the amount of time of the deviation.

Other shortcomings of present dispensing or access devices include the inability of a patient to take a medication early if he or she will not be able to take the dose at the scheduled time. For example, if medication is to be taken once every 4 hours, and a patient is planning to leave their house fifteen minutes prior to the next dose period, then it may be proper for the patient to take the dose early. In fact, the patient may even wish to take the dose with them. However, it is generally not possible to do this with present devices while remaining on the appropriate timing schedule.

There is a need therefore, for a medication dispensing device that is easy to use by elderly and disabled individuals, and adequately prevents overdosage. Specifically, there is a need for a device that dispenses medication doses and collects untaken doses so as to make them unavailable to the patient.

There is a further need for a medication dispensing device which provides ample feedback to a patient's inquiry regarding the status of doses taken or not taken, as well as when the next dose will be made available.

There is also a need for a medication dispensing device which is capable of alerting individuals other than the patient of problems that arise in connection with the administration of medication.

SUMMARY OF THE INVENTION

In a preferred embodiment of the invention, the device prevents prolonged underdosage by monitoring whether medication is both requested by the patient and appropriately dispensed. The device prevents overdosage by storing pills which were not taken on time so that such medications cannot be taken or otherwise improperly used such as by distribution to others. The device monitors compliance with a dispensing schedule and alerts caregivers when non-compliance has occurred and personal intervention by a caregiver is advised. The dispenser is easily operated by the visually impaired, the hearing impaired and persons having low manual dexterity abilities, and provides information to the patient regarding medication regimens, such as the next dosage time, and the previous dosage time. Instructions such as whether to take certain medications with food, or whether replacement or refill cartridges should be ordered are also provided.

In one embodiment of the invention, the pill dispensing device is portable, with all medications which are to be taken at the same time grouped together in a prepackaged container. An audible signal and visual cue signals the patient when it is time to take the medication. Under normal conditions the medication is dispensed responsive to a signal from a push button switch. If medications are not dispensed at the proper time then medications which were not timely taken are diverted to a storage compartment to prevent their improper use by the patient. In addition, the event is recorded and a pharmacist, physician, or other caregiver is notified so that appropriate action may be taken.

The pill dispensing device of the invention is interactive in its ability to respond to a wide variety of situations, and is flexible in its ability to operate in response to the patient's scheduling constraints.

BRIEF DESCRIPTION OF THE DRAWINGS

The description of the invention may be further understood with reference to the accompanying drawings in which.

DETAILED DESCRIPTION OF THE INVENTION

The following description of the illustrated embodiments includes a description of the structure of the illustrated devices, a description of the operation of the embodiments, and concludes with a description of an exemplary program for implementing the system of the invention.

Figure 1:
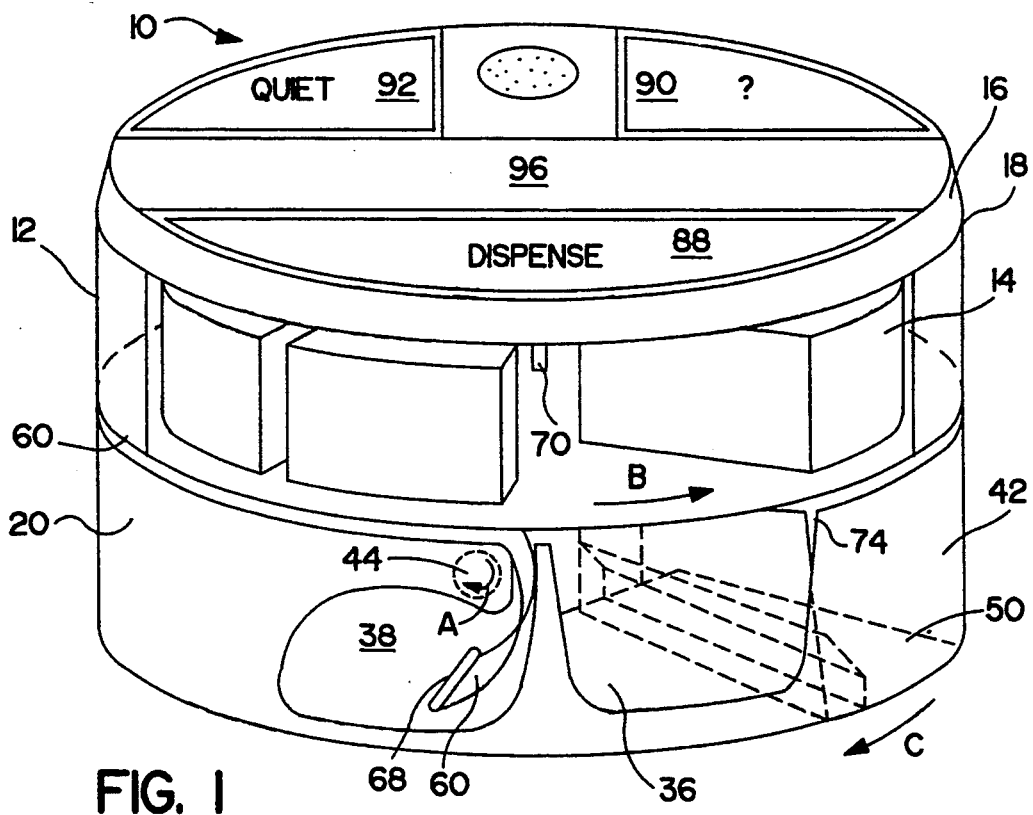
FIG. 1 shows an isometric view of a pill device of the invention.
Figure 2:
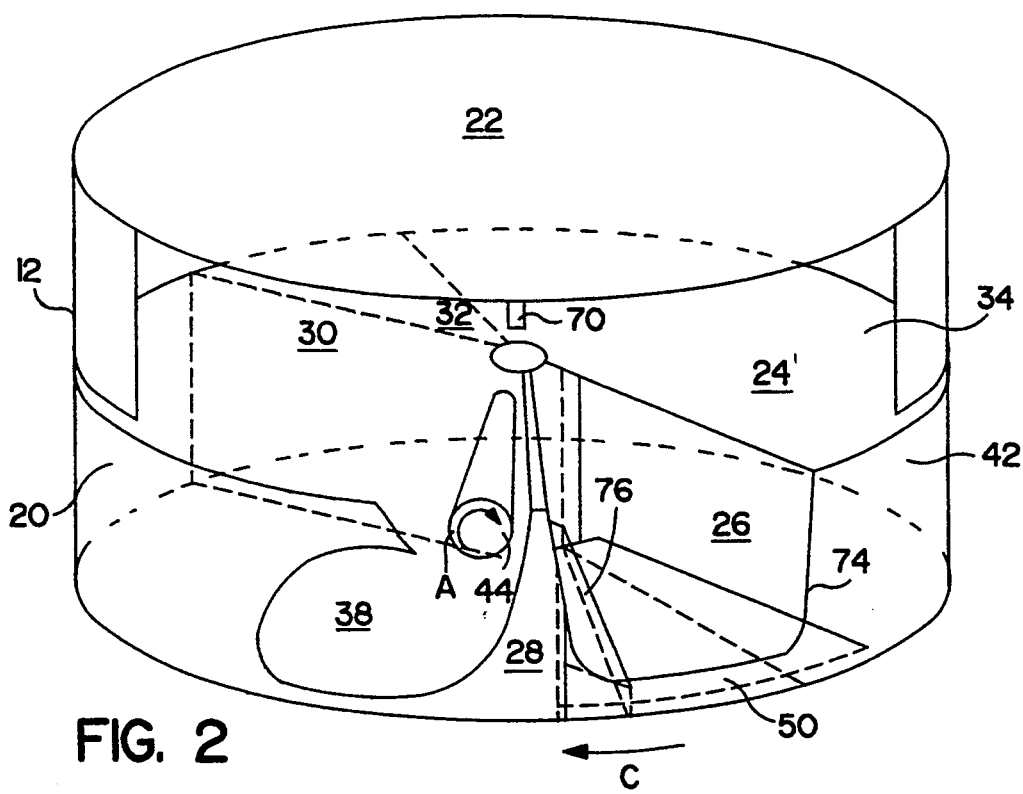
FIG. 2 shows an isometric view of the housing of the device shown in FIG. 1 with the overdosage protection drawer open.
Figure 4:
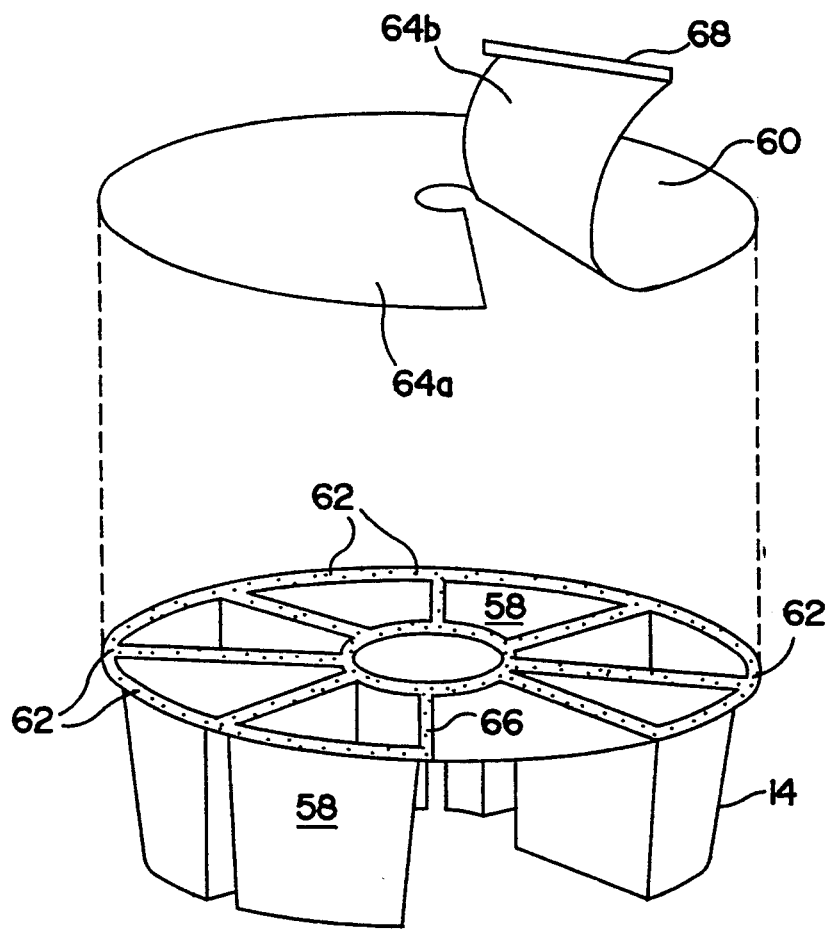
FIG. 4 shows an exploded view of the pill cartridge shown in FIG. 3.
Figure 5:
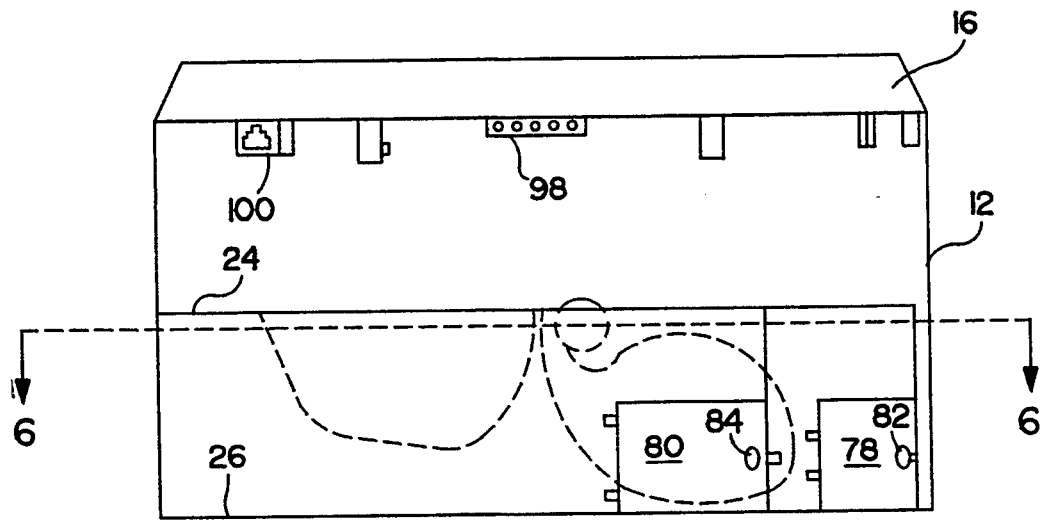
FIG. 5 shows a rear view of the device shown in FIG. 1.
Figure 6:
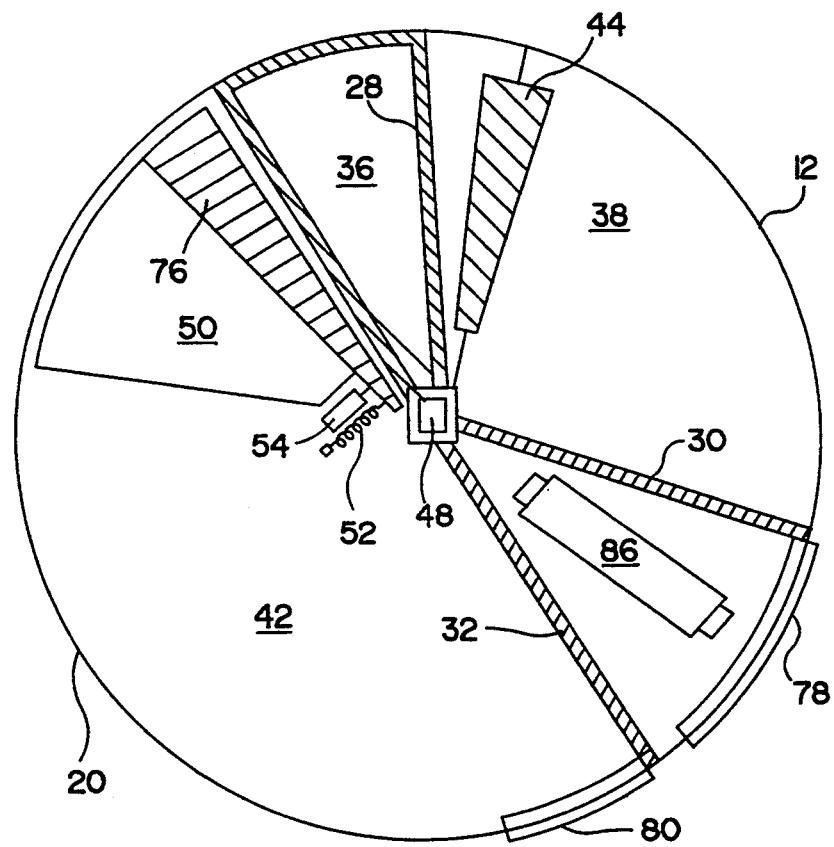
FIG. 6 shows a sectional view of the device of FIG. 5 taken along line 6—6 from above.

The illustrated devices:

As shown in FIGS. 1 through 9 an embodiment of a pill dispenser 10 of the invention includes a housing 12, a pill cartridge 14 removably inserted within the housing 12, and a patient interface unit 16 mounted on the top surface 18 of the housing 12. The housing 12 includes an cylindrical wall 20, a top wall 22, a middle wall 24, a bottom wall 26, and first, second and third inner partitions 28,30,32. The housing 12 defines a cartridge receiving area 34, a dispensed pill passage area 36, a cartridge cover receiving area 38, a power supply area 40, and an expired pill receiving area 42. The housing 12 contains a tapered drive wheel 44, a power supply 46, a motor 48, a radially rotatable overdosage protection drawer 50, an overdosage protection spring 52, and an overdosage protection solenoid 54 as shown in FIGS. 1, 2 and 6.

The cartridge receiving area 34 is defined by the cylindrical 20, top 22 and middle 24 walls of the housing 12. The dispensed pill passage area 36 is defined by the first partition 28, the drawer 50, the cylindrical wall 20, the middle wall 24, and an opening 56 in the bottom wall 26 of the housing 12. The cartridge cover receiving area 38 is defined by the first and second partitions 28,30, and the cylindrical 20, bottom 26 and middle 24 walls of the housing 12. The power supply area 40 is defined by the second and third partitions 30,32, and the cylindrical 20, bottom 26 and middle 24 walls of the housing 12. The expired pill receiving area 42 is defined by the drawer 50, the third partition 32, and the cylindrical 20, bottom 26 and middle 24 walls of the housing 12.

Figure 3:
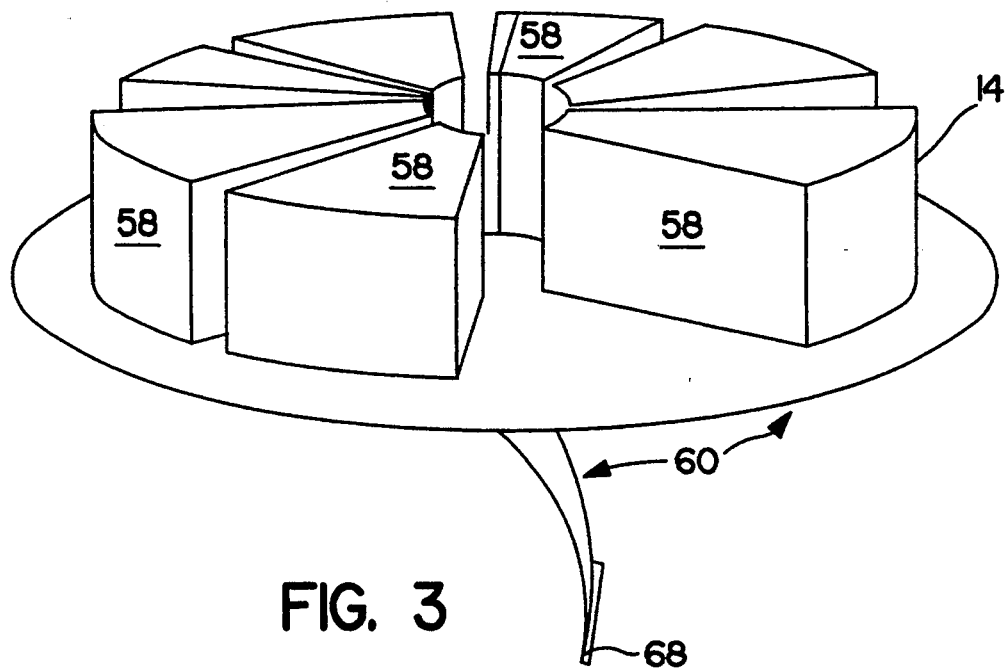
FIG. 3 shows an isometric view of the pill cartridge of the device of FIG. 1.

As shown in FIGS. 1, 3 and 4, the cartridge 14 includes several pill containment cavities 58 and a cartridge cover 60 releasably adhered to one side of the cartridge with a releasable adherent 62 (such as a pressure sensitive adhesive), such that the pill containment cavities 58 are sealed thereby. The cartridge cover 60 is generally circular and includes two end portions 64a, 64b. The first end portion 64a of the cartridge cover 60 is permanently adhered to the cartridge 14 with a permanent adherent 66 as shown in FIG. 4, and the second end portion 64b includes a securing tab 68 on its leading edge.

The housing 12 also includes a guide key 70 which aids in the insertion of the cartridge 14 by ensuring proper alignment of the cartridge 14 with respect to the housing 12. When the cartridge 14 is inserted into the housing 12, the cartridge cover 60 is placed in contact with the drive wheel 44, and the securing tab 68 is positioned within the cartridge cover receiving area 38. The cartridge 14 may be made of an ultraviolet light filtering material, and the cover 60 may be made of a thin metal foil. When adhered to the cartridge 14, the cover 60 seals out dirt, moisture, and other potential contaminants.

The tapered drive wheel 44 is in communication with the cartridge cover 60 such that when the drive wheel 44 rotates in direction A (as depicted in FIGS. 1 and 2), the cartridge cover 60 is drawn toward the drive wheel 44 thus causing the cartridge 14 to rotate in direction B (as depicted in FIGS. 1 and 3). As the cartridge cover 60 passes over the drive wheel 44, the cover 60 is separated from the cartridge 14 and the cover 60 is directed into the cartridge cover receiving area 38. The drive wheel 44 is tapered to conform to the circular shape of the cartridge cover 60, and is driven by the motor 48 under the direction of the controller 72 as discussed below. The motor 48 and the controller 72 are powered by the power supply 46. The wheel 44 may include frictional material to facilitate engagement with the cover 60. Alternatively, the cover 60 may include frictional adhesive strips on the surface of the cover for facilitating engagement with the drive wheel 44. The housing 12 may also include an opening 74 in its cylindrical wall 20 for assisting the user in inserting and removing the pill cartridge 14.

Figure 11:
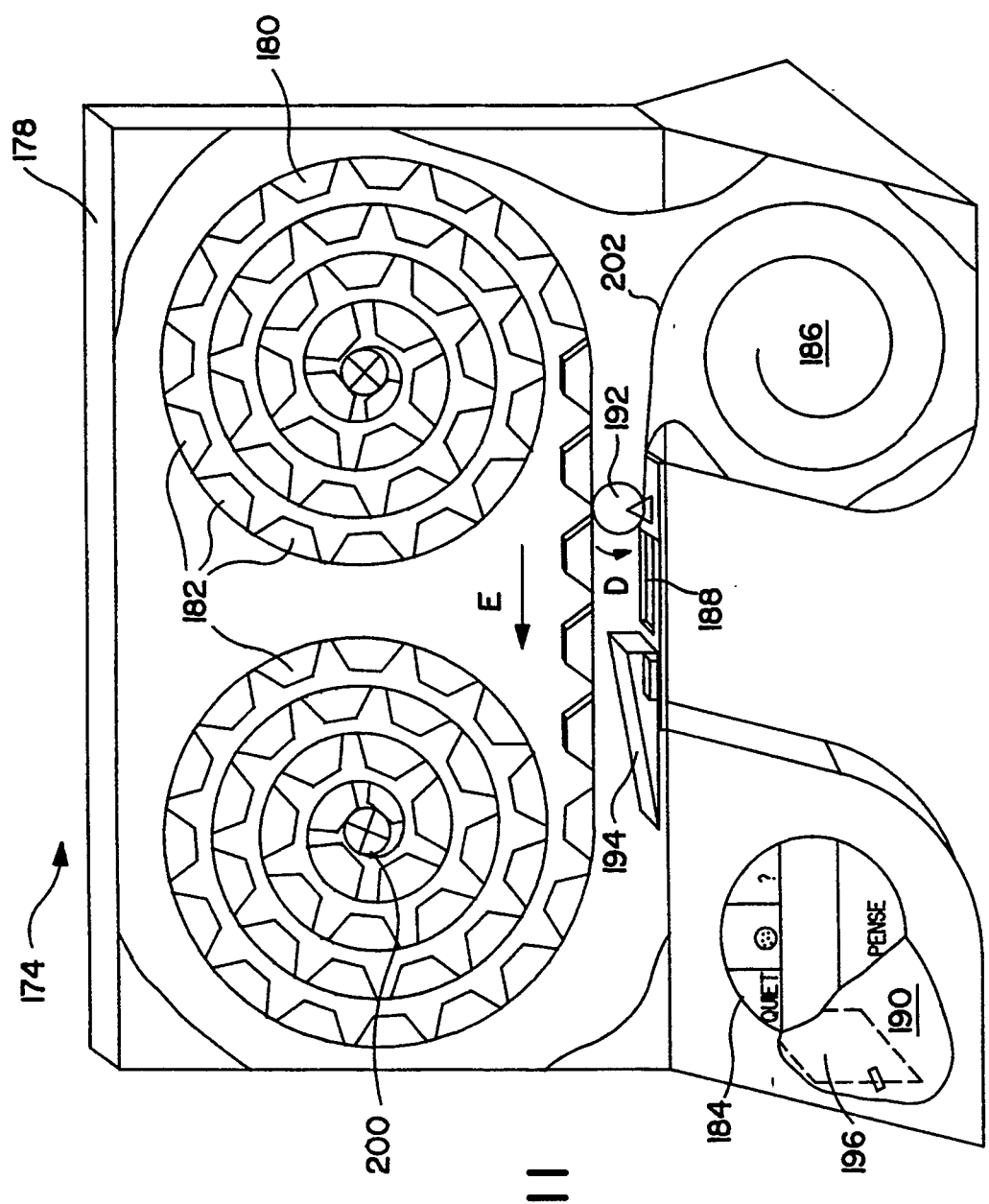
FIG. 11 shows a pill device of a non-portable embodiment of the invention.

In certain embodiments, when insertion is complete the partition closes to engage the cover's leading edge between the drive wheel 44 and the surface of the partition top 15b, forming a nip as shown in FIG. 11. The coefficient of friction between the cover 60 and the drive wheel 44 is greater than the coefficient of friction between the cover 60 and the surface of the partition 15b. As the drive wheel 44 turns, the cover 60 is pulled through the nip. As the cover 60 is pulled through the nip, the cartridge 14 is rotated.

When the cartridge 14 rotates, an uncovered pill cavity 58 of the cartridge 14 is positioned above the dispensed pill passage area 36, and pills contained within the cavity 58 are then free to fall through the dispensed pill passage area 36, through the bottom wall 26 of the housing 12, and into a cup or hand placed beneath the housing 12. The permanent adhesive 66 is located at the trailing edge of the last containment cavity 58 to be rotated over the pill passage area 36.

Also contained within the housing 12 is an overdosage protection unit which includes the radially rotatable drawer 50, the spring 52 and the solenoid 54. When the solenoid 54 is energized the drawer 50 is rotated in direction C, as shown in FIGS. 1, 2 and 6, pills falling from the cartridge 14 are directed onto the sloped surface 76 of the drawer 50 and into the expired pill containment area 42 within the housing 12. When the solenoid 54 in de-energized, the spring 52 returns the drawer 50 to its non-rotated position. The drawer 50 is shown in FIGS. 1 and 6 in its non-rotated position, and shown in FIG. 2 in its rotated position. The solenoid 54 is energized by the power supply 46 under the direction of the controller 72 as discussed below. Optionally, the overdosage protection unit may include a position sensor, such an LED and receiver pair to indicate the relative position of the overdosage protection drawer, thus determining whether or not the drawer is open, i.e., whether the drawer is directly below the pill passage area.

As shown in FIGS. 5 and 6, the cylindrical wall 20 of the housing 12 further includes a power supply access door 78 and an expired pill receiving area access door 80. Each of these doors may include locks 82, 84 as shown in FIG. 5. The expired pill access door 80 permits removal of untaken pills which are contained within the expired pill receiving area 42. In alternative embodiments, the access door 80 may be positioned in either of middle wall 24 or bottom wall 26. The power supply access door 78 permits access to a battery 86 which may be periodically replaced or recharged.

Figure 7:
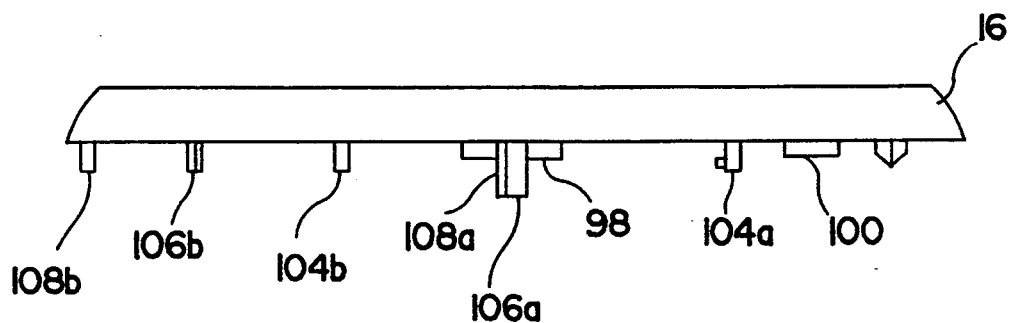
FIG. 7 shows a side view of the interface unit of the device shown in FIG. 1.
Figure 8:
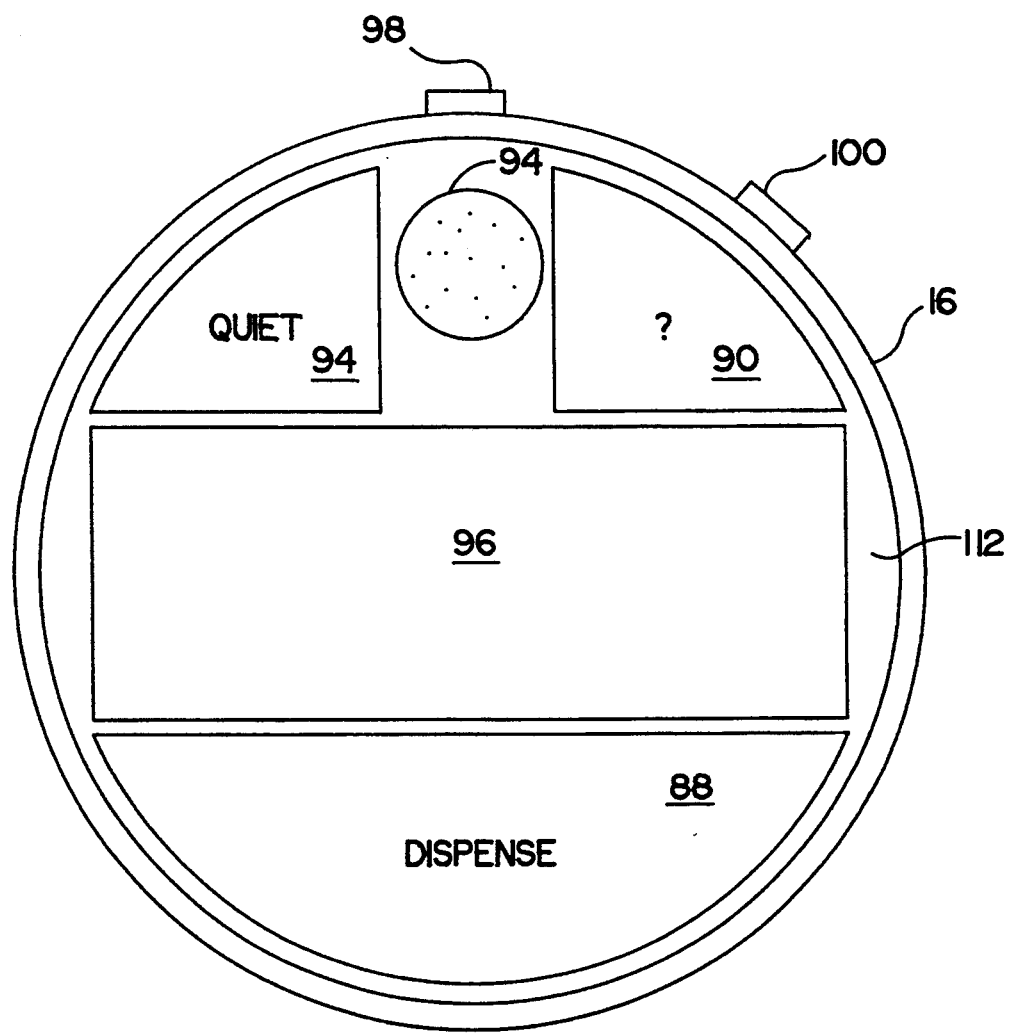
FIG. 8 shows a top view of the interface unit of the device shown in FIG. 7.
Figure 9:
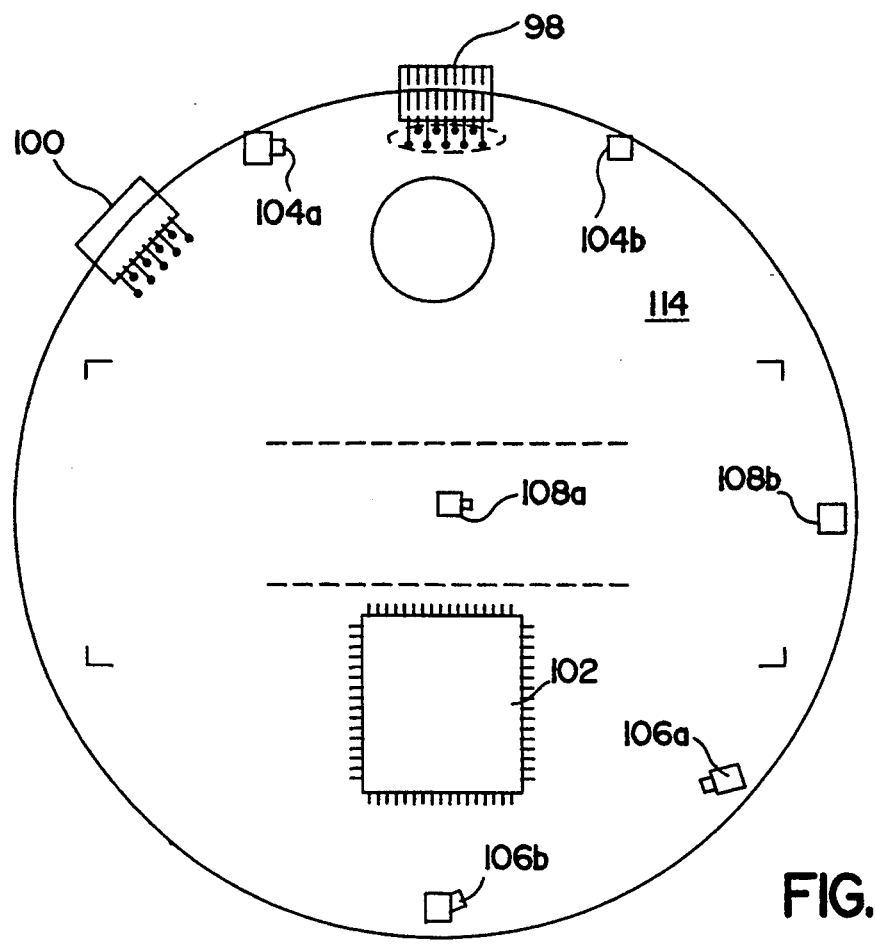
FIG. 9 shows a bottom view of the interface unit shown in FIG. 7.

As shown in FIGS. 1, and 8, the patient interface unit 16 includes three push switches 88, 90, 92, a speaker 94, a two row liquid crystal display (LCD) unit 96, a port 98 for connecting the interface unit 16 to a programming device and a phone line port 100 for connection to a standard telephone unit connector plug. As shown in FIGS. 5, 7 and 9 the patient interface unit 16 also includes a microprocessor 102 and three light emitting diode (LED) and receiver pairs 104, 106, 108. The first pair 104 detects whether the cartridge 14 is fully inserted within the housing 12. Upon removal of the cartridge 14 from the housing 12, the second pair 106 detects whether the cartridge 14 has been fully removed from the housing 12. The LED of the second pair 106 is mounted on the insertion guide key 70 which is formed as part of the housing 12.

The third pair 108 detects whether a cavity 58 is positioned between the LED and the receiver. The information from the third pair 108 is used to index the rotation of the cartridge 14 such that one cavity is positioned above the passage 36 each time the cartridge 14 is rotated. The receiver, or photoeye, of the third pair 108 detects the trailing edge of the pill cavities 58 as they rotate between the LED and the receiver.

The three push switches 88, 90, 92, the LCD display 96, and the speaker 94 are mounted on one side 110 of a printed circuit board 112 as shown in FIG. 8. One or more of the push switches may be illuminated. The microprocessor 102, the LED/receiver pairs 104, 106, 108, and the ports 98, 100 are mounted on the opposite side 114 of the printed circuit board 112 as shown in FIG. 9. The serial port 98 may be a female nine pin "D type" serial port connector or a 5 pin in-line connector, and the phone line port 100 is a standard telephone modem port. All switch inputs are debounced in accordance with the art.

Figure 10:
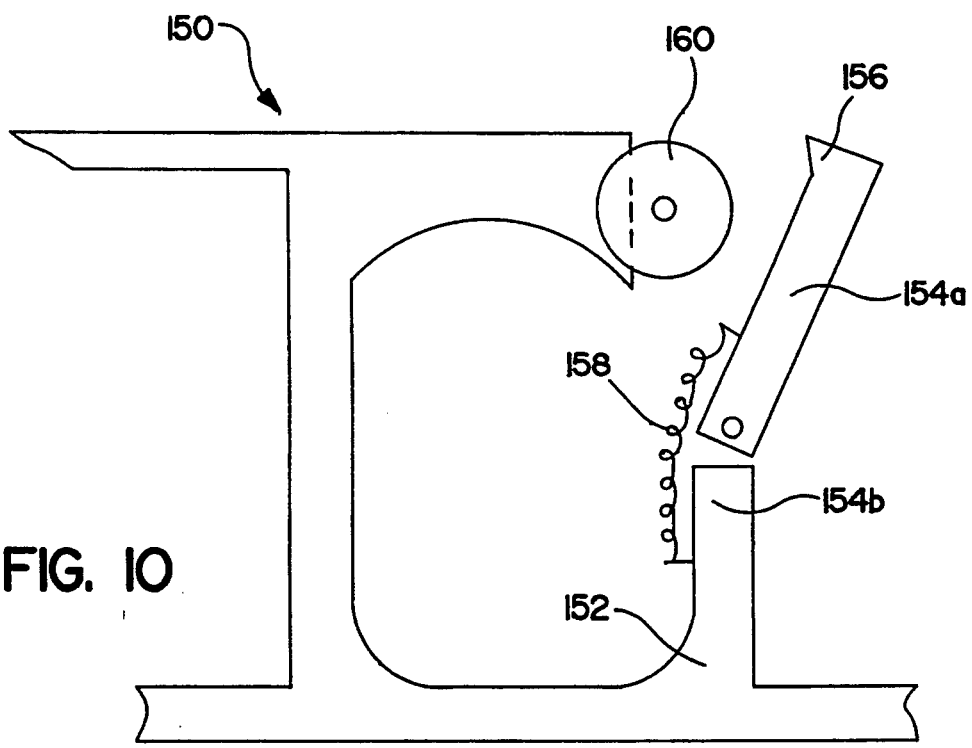
FIG. 10 shows a portion of a drive unit of the invention.

FIG. 10 shows an embodiment of a drive unit of the invention 150. Specifically, the first partition 152 is subdivided into two hinged portions 154a, 154b, the upper one of which 154a includes an angled top 156. The first partition 152 also includes a biasing spring 158 which urges the angled top 156 of the upper hinged portion 154a against the drive wheel 160. This enhances the cartridge cover drive capabilities of the drive unit. Alternatively the upper hinged portion 154a could be selectively urged against the drive wheel 160 using, for example, a solenoid.

To accomplish the drive capabilities of the drive unit, the cover must be held against the wheel with sufficient force to prevent relative motion (e.g., slipping) between the wheel and the cover. The wheel may include a frictional coating or covering to prevent slipping, or alternatively, frictional strips may be disposed on the cover side that is facing the wheel to prevent slipping.

FIG. 11 shows a non-portable embodiment of the invention 174 including a housing 178, a pill cartridge strip 180 having a number of pill containment cavities 182, and a patient interface unit 184. The housing 178 generally defines a pill cartridge strip cover receiving area 186, a dispensed pill passage area 188, and an expired pill receiving area 190. The housing 178 further includes a drive wheel 192, an overdosage protection ramp 194, and an expired pill access door 196. In alternative embodiments, the drive wheel 192 may cooperate with a second wheel to pinch the strip 180 therebetween.

As the drive wheel 192 is rotated in the direction depicted by "D" in FIG. 11, the pill cartridge strip 180 moves in the directions depicted by "E". Alternatively, the take-up reel 200 itself may be powered as well. In either case, as the cartridge strip 180 moves away from the wheel 192, medications from the uncovered pill containment cavities 182 fall through the dispensed pill passage area 188 and the pill cartridge strip cover 202 is directed toward the cartridge cover receiving area 186.

Power is provided either by use of a battery as discussed above in connection with the embodiment shown in FIGS. 1 through 10, or a voltage regulator and an AC power cord may be included such that the cord can be connected to a standard 120 volt AC outlet to supply power to the unit. The patient interface unit 184 operates as discussed below with reference to FIGS. 12-14.

Figure 12:
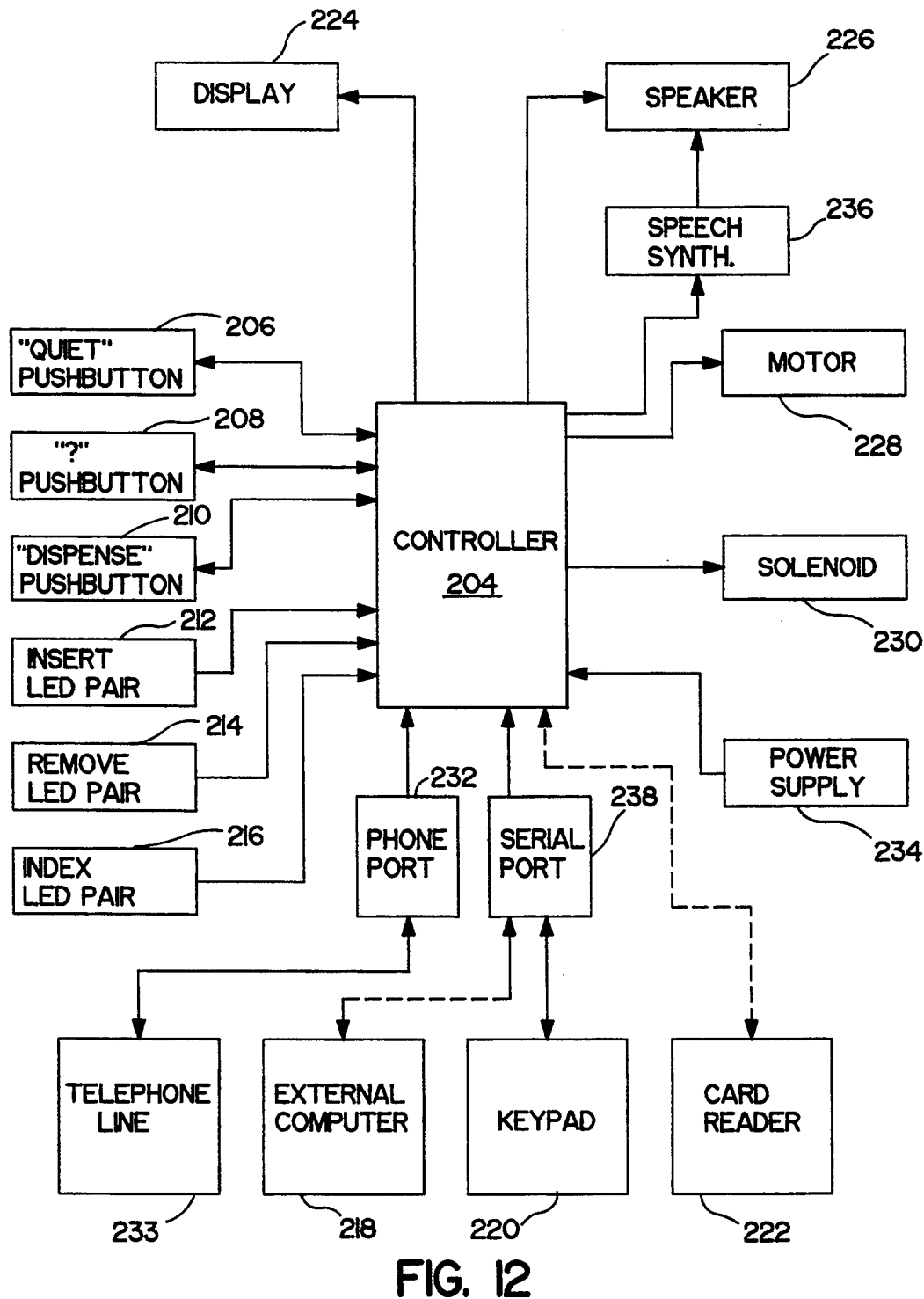
FIG. 12 shows diagrammatic representation of a control system of the invention.

Operation:

The controller 204 includes a microprocessor and, as shown in FIG. 12, receives input signals from the three pushbutton switches 206, 208, 210, the three LED/receiver pairs 212, 214, 216, and any of a number of external programming devices such as a computer 218, an external keyboard 220 or a card reader 222. The controller 204 sends output signals to the display 224, the illuminated pushbuttons 206, 208, 210, the speaker 226, the motor 228, the overdosage protection solenoid 230, and the phone line port 232 for connection to a telephone line 233. The controller 204, as well as the motor 228, solenoid 230, display 224 and speaker 226, are all powered by the power supply 234. As shown in FIG. 12 a speech synthesizer 236 may be used in connection with the speaker 226 to further enhance its audio signaling capabilities. Reports and other messages may be sent via the phone line port 232 through telephone lines to a receiving unit (at, for example, a doctor's office or a relative's home) which monitors the reports.

The controller processes the inputs and controls the outputs responsive to a predetermined program which may be loaded into the device by any of the following exemplary methods. The device may include a serial port 238 (or any other type of port) which may be connected to an external computer 218. The program could be initialized in the external computer and later loaded into the device via the serial port. Alternatively the device could be connected to an external keyboard or keypad 220 and the program could be initialized via entering data through the keypad. The display 224 may be utilized in this process to provide feedback to the person initializing the program (such as prompts for inputing data into the keypad). Other methods of loading program information into the device include the use of the card reader 222 or connection of the phone line port 232 to a telephone line for remote programming. Optionally, the device may include a signal transmitter which communicates with a remote receiver.

The operation of a device of the invention may be described with reference to several operational states: 1) insertion of a pill cartridge state, 2) an idle state, 3) a pre-dispense state, 4) a dispense state, 5) a post-dispense state, 6) a remove pill cartridge state, 7) a report state, and 8) a programming state.

Generally, for each cavity there is a programmed time of day when the patient may push the DISPENSE button and medication will be dispensed. Additionally, access may be provided for relatively short periods of time before and after the above time for each cavity. The periods of time before and after are also preprogrammed. At any other time, pushing the DISPENSE button will not cause the device to dispense the pills. Pills not timely taken are discharged into an area not accessible to the patient.

1) insertion state:

In the insertion state, the patient inserts the prefilled pill cartridge into the cartridge receiving area of the housing with the leading edge of the cover disk in the slot between the drive wheel and the first partition. This state may be initiated by the remove pill cartridge state or the program state.

In this state the message "Insert a new pill cartridge" is displayed flashing on the LCD display and an audible signal is repeated with its volume incrementally increasing. If the QUIET pushbutton is pressed then the audible signal stops, but the light continues to flash. When the insertion LED/receiver pair detects the presence of the leading edge of the pill cartridge cover, then the display will stop flashing and will change to "Insertion complete". An audible signal will be sounded.

In the present embodiment of the invention a portion of the first partition moves to firmly engage the drive wheel against the cover. The drive wheel is caused to rotate responsive to the output of the insertion LED/receiver pair which senses the presence of the pill cartridge in the housing. The drive wheel engages the cartridge cover by moving the first partition against the cover and the drive wheel forming a nip. The drive wheel rotates the pill cartridge until the leading edge of the first cavity is sensed by the rotation LED/receiver pair. The output of this LED pair indicates that the cover is properly engaged in the nip. The controller then directs the speaker and display outputs to indicate that insertion is complete, such as by displaying the message "Insertion is complete".

2) idle state:

In the idle (or default) state the microprocessor monitors the internal clock as well as several of the inputs. The index, insert, and removal complete photodetectors are monitored for changes. If such input signals change then a failure condition is reported by displaying "System failure" on the display and sounding an audible signal. The battery power is monitored, and if it falls below a threshold level, then the message "Replace battery" is displayed together with an audible signal.

If the inquiry pushbutton switch is pressed, then the following repeating sequence of exemplary messages is displayed: "Your medication is to be taken at 1:00 pm", "Medication must be taken before 1:30 pm", "Your last medication was taken at 11:00 am" and optionally "You have missed your medication" as appropriate.

If the DISPENSE pushbutton is pressed, then the messages "It is not time to take your medication now" is displayed, and is followed by the sequence noted above regarding the next and previous medication times. This sequence repeats for a period of time and an audible signal is produced. The occurrence of this inquiry may be recorded for purposes of gauging the level of confusion or anxiety of the patient. This information may be evaluated by the program in deciding whether to honor a request for medication in the pre-dispense state. It is desirable to permit early access (to accommodate a patient's schedule) only for patients who have not indicated that they are confused by repeatedly pressing the DISPENSE pushbutton at inappropriate times.

3) pre-dispense state:

The program is in the pre-dispense state when the current time is within the pre-dispense window time, for example ½ hour before the preset dispense time. The unit will dispense the contents of a pill cavity if the DISPENSE button is pressed during the predispense window time and if there are no prior alarm conditions, such as an event that would cause the system failure message to be displayed.

4) dispense state:

The dispense state is initialized when the DISPENSE button is pressed and the program is in the pre-dispense or post-dispense state, as described below. When the DISPENSE button is pressed it stops flashing in the event that it had been flashing, and the audible signal is silenced. The drive wheel is then rotated which simultaneously draws the cover off of the cartridge and rotates the cartridge exposing the next cavity. The contents of the cavity then fall through the pill passage area. The pills may fall through this hole into a container provided by the patient. The output of the "index complete" LED receiver pair signals that the cartridge cavity has been sufficiently rotated over the pill passage area to ensure that all of the contents of the cavity have been removed. The drive wheel is then stopped.

5) post-dispense state:

The program is in the post-dispense state when the current time is within the post-dispense window time, for example 1 hour after the preset dispense time. The DISPENSE pushbutton is illuminated on and off repeatedly and the speaker outputs an audible signal. The messages "Take your medication", "Push the lighted DISPENSE button", and "Set the dispenser on a flat surface" are displayed flashing.

The unit will dispense the contents of a pill cavity if the DISPENSE pushbutton is pressed during the post-dispense window time and if there are no prior alarm conditions such as a system failure.

If the DISPENSE button is not pressed then the audible signal continues for twenty seconds. After one minute, the signal again continues for twenty seconds with the volume of the speaker output increased. This cycle continues for five minutes. If, after five minutes, the button is still not pressed, then the audible signals are delivered for the first twenty seconds of each five minutes until the dispense window has lapsed at which time the signalling and message displays cease. Each time, the volume of the speaker is increased. In the later stages of the post window of time, the exemplary message "Medication must be taken before 1:30 pm" may be displayed. The initial delay (of five minutes) may be a function of the post window time. If the QUIET button is pressed then the audible signal will stop, although the messages will continue to be displayed. Certain of the messages may cease when, for example, 95% of the post window time has expired.

If the ,schedule is not met by the patient, i.e., if the patient does not timely press the DISPENSE pushbutton, then the controller records that the cavity was not timely emptied. The next time the DISPENSE pushbutton is pressed to dispense the next dosage of medication, the overdosage protection drawer will be moved into position within the pill passage area. The cartridge will then rotate such that the previous cavity is positioned over the pill passage area, and the untaken pills will fall into the overdosage protection drawer. The number of cavities which are rejected are queued and identified with an associated time and date for later reporting. The drawer will then close, and the cartridge will again rotate to permit proper dispensing of the next dosage.

If the reject drawer includes a position sensor, and if the output of this sensor changes state, then the message "System failure" is displayed along with an audible signal.

6) removal state:

If the cavity to have recently had its contents discharged is the last cavity in the cartridge, then the remove pill cartridge state is initiated. This occurs once the drive motor has stopped, and the preset pill cartridge loading time has been reached. The backing plate will move away from the drive wheel opening the nip and releasing the cover disk. A soft (quiet) audible signal will be sounded and the message "Remove pill cartridge" will be displayed flashing on the LCD display. After approximately 5 minutes, time enough to allow the patient to take the last set of pills, the audible signal will again be sounded and the message will repeat. This sequence will repeat with increasing volume until the pill cartridge disk is removed or the QUIET pushbutton is pressed.

The pill cartridge disk is removed by grasping it and pulling it from the device cavity. This simultaneously pulls the cover paper from the paper cavity. When this is completed, as sensed by the removal completed photoeye, then the "insert pill cartridge" state is initiated.

If the QUIET button is pressed the audible signal will cease, however, the message display will continue to flash.

7) report state:

In the report state the device reports information. The dispenser will be connected, either physically by wires or remotely by infrared light or radio waves, to the telephone line in the evening. At a preprogrammed time, e.g., between 11 PM and 5 AM, the microprocessor will call, via the on board modem, a preprogrammed phone number. Status information concerning medications which were not taken at the proper time will be transmitted to a receiving computer. A printer may also be connected to the serial port to provide the patient with a printout of the report.

This state may be initiated by a programmed pushbutton or the controller itself as part of the program. For example, at a time based on the device's serial number the device may send the report over the telephone lines through the phone line port. After the connection is made information such as the following may be transmitted: the serial number of the device, the time and day each cavity was programmed to dispense, the time and day each cavity was dispensed, the time and day the QUIET button was pressed, the time and day of removal of the pill cartridge, the time and day of insertion of the pill cartridge, the time and day that medication was missed, the time and day the "?" pushbutton was pressed, the time and day of engagement of the overdosage protection unit, and any other information concerning the status of the system.

Figure 13:
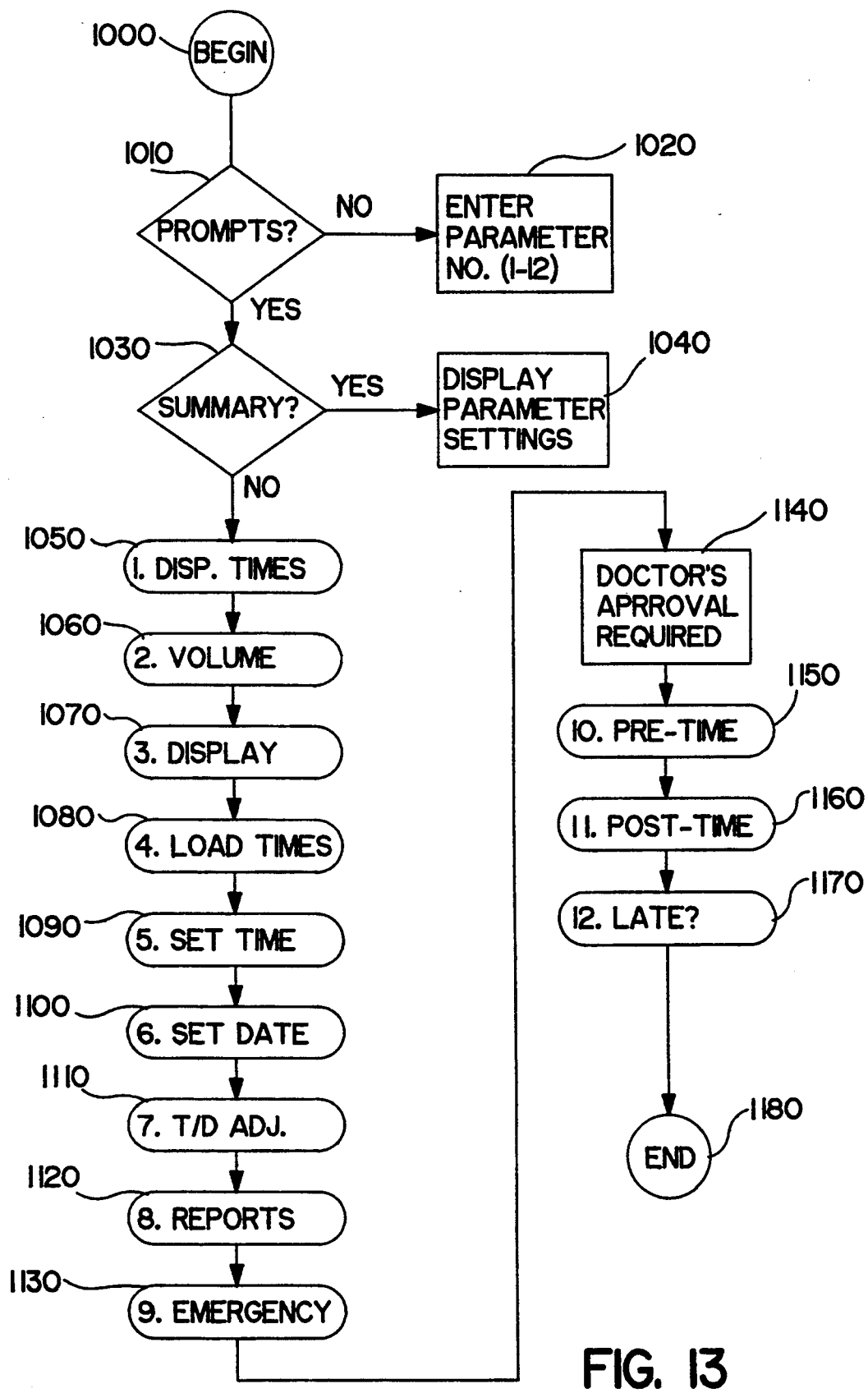
FIG. 13 shows a flowchart of the set-up procedure for an embodiment of the invention.

8) programming state,

FIG. 13 shows the procedural steps for initializing a system of the invention. The initialization (or set-up) program may be commenced from the main operational program (FIGS. 14A-14D), or it may be executed at the time when a new cartridge is inserted into a device of the invention.

The set-up program begins (step 1000) by displaying the message "Set-up with prompts? 1) yes or 2) no" on the LCD display (step 1010). If the user responds in the negative (through input via a keypad attached to the serial port) then the program awaits further input (step 1020) regarding which parameter (1-12) the user wishes to change. This is a shorter set-up procedure appropriate for changing a few parameters only. Parameters 1-12 correspond to steps 1050-1130 and 1150-1170 respectively.

If the user responds to the message associated with step 1010 in the affirmative, then another prompt is displayed (step 1030) asking whether the user would like to view (on the LCD display) a summary of the current parameter settings (step 1040). Otherwise, the full set-up procedure (steps 1050-1170) is executed. Each of the subroutines identified in the following steps is executed using prompts displayed on the LCD display and input from a keypad received through the serial port. Alternatively an external display and keyboard system (such as another computer) may be connected to the device through the serial port to provide output to the programmer.

In step 1050 the dispense times for each cartridge cavity are sequentially programmed into the device. The user is prompted with messages such as "Current setting for cavity #1 is 8:30 am. Enter new time for cavity #1." The DISPENSE button may be used as the enter key for entering each new time.

In step 1060 the volume for the speaker may be adjusted. There may be several volume settings (e.g., 1–10) and the associated number may be entered, or the user may be permitted to incrementally change the volume by repeatedly pressing one of two buttons or keys (one for increasing and the other for decreasing). Following each change in setting the speaker may output a signal at the new volume and the user may be permitted to further change the volume as desired.

The length of time (e.g., in seconds) that a message should appear on the LCD display for a patient to read the message may then be changed (step 1070). Again, either a setting number (1–10) may be entered or the time may be changed via incremental input. Following each change the LCD display should display a message for the new period of time, and readjustment should be permitted until the user indicates that the setting no longer needs adjustment.

Next the user may change the times (and/or dates) at which the cartridge should be reloaded (step 1080). This information may be actual times and dates, or it may be dependant on the dispense time of the last cartridge cavity (such as the following evening or morning).

The user may then change the current time (step 1090) and the current date (step 1100). This may be necessary on occasion, for example, when the battery is replaced. Adjustments to the current time and date may be further made (step 1110) by entering data regarding daylight savings time and even time zone information if necessary.

Information may then be supplied regarding where, when and how reports are to be sent to individuals other than the patient (step 1120). For example, in one embodiment a phone number may be entered together with a time of day for sending reports via telephone lines. Preferably the report procedure, together with the new settings, should be tested during this subroutine.

Information similar to that discussed above may then be entered (step 1130) regarding who to contact (and how) in the event of an emergency. Again this procedure should be tested.

The remaining set-up parameters should be changed only with the approval of a caregiver, such as a doctor. Accordingly, in step 1140 a message to this effect is displayed on the LCD display. In alternative embodiments passwords or codes may be employed to safeguard against the occurrence of unauthorized changes.

The pre-dispense time period, if any, may then be changed for each cavity (step 1150), followed by the post-dispense time period, if any, for each cavity (step 1160). In step 1170, information may be entered regarding whether the dispensation schedule should be adjusted if certain medications are taken late. The dispense time for certain cavities may therefore be dependant on the actual dispense time of previous medications, independent of the schedule for the remaining cavities. The set-up program then ends (step 1180).

Implementation:

A program for implementing a pill dispensing device of the invention is described as follows with reference to FIGS. 14A–14D. Software flags are used to enable or disable the execution of subroutines.

Figure 14A:
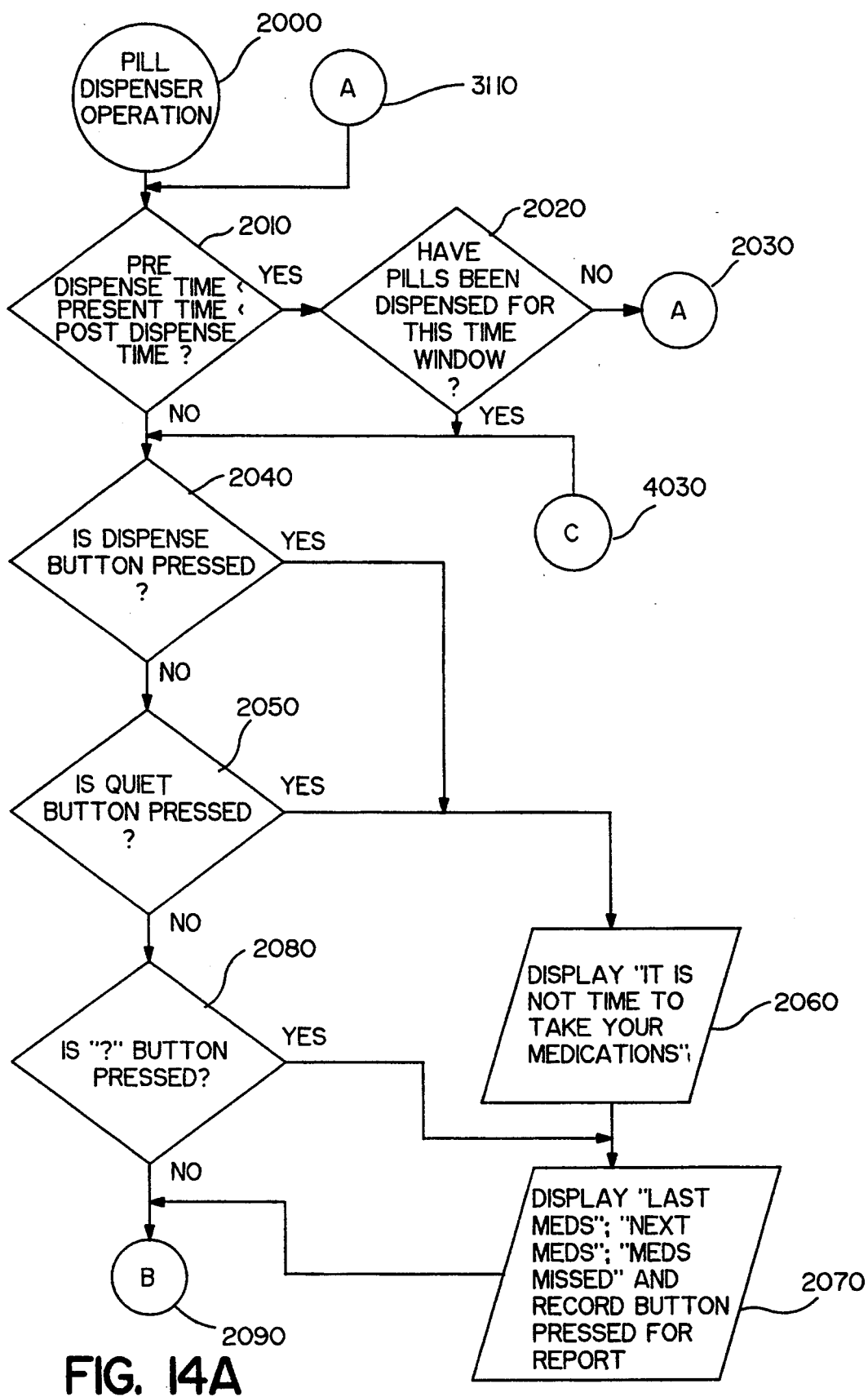
FIGS. 14A–14D show a flowchart of the operational procedure for an embodiment of the invention.
Figure 14B:
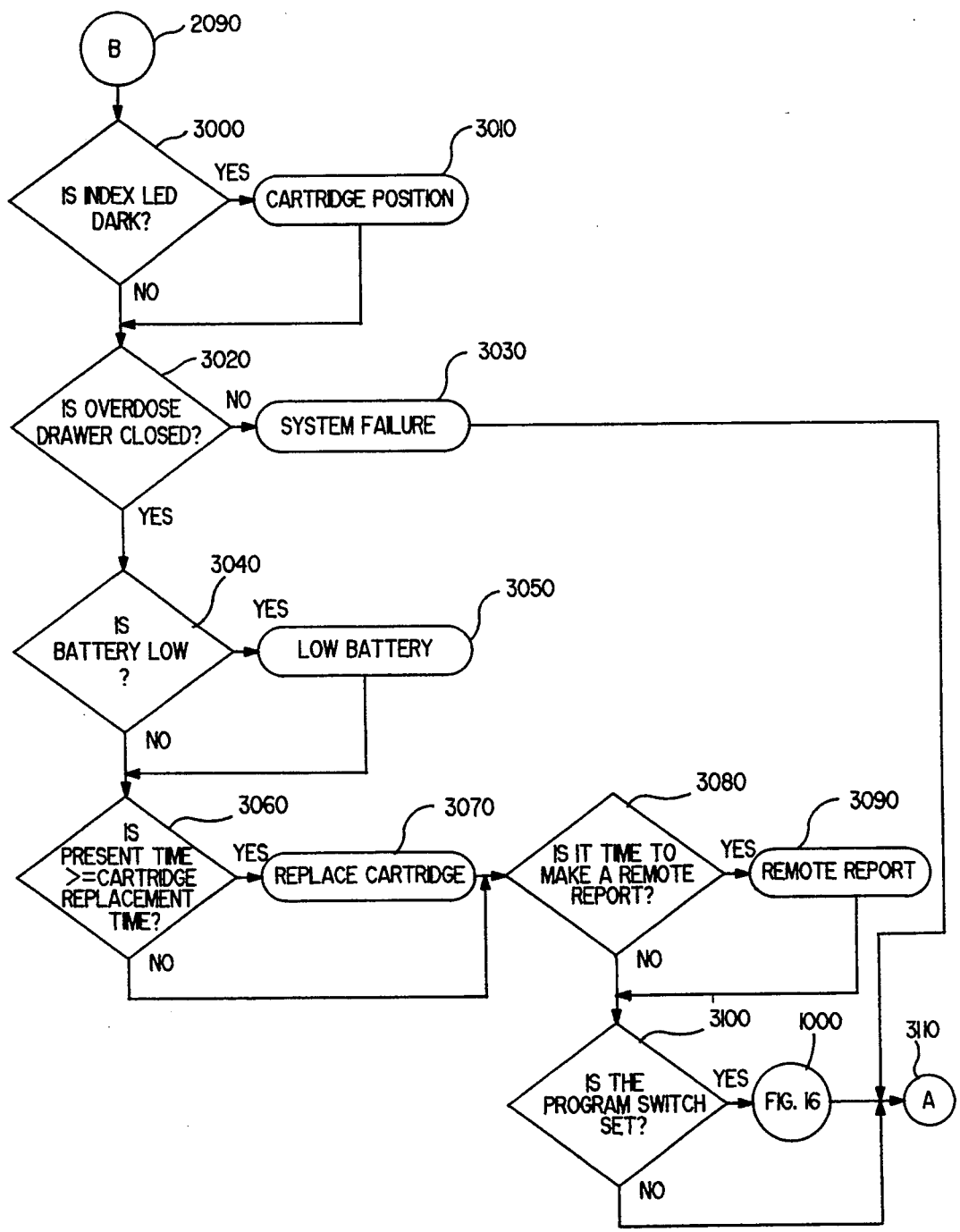

As shown in FIGS. 14A and 14B the program comprises a main routine beginning with step 2000. A decision is made by the controller whether the present time is greater then the predispense time window or less than the post dispense time window (step 2010). If so then it is decided whether the pills for this dispense time window have been dispensed (step 2020). If so then the main routine continues to step 2040. If the pills have not been dispensed, then the pill dispense subroutine (step 2030) is executed. This subroutine may return to the main routine from steps 4030, 3110 or 2090.

If the present time is less than the predispense time or greater than the post dispense time, then the program decides successively whether the DISPENSE, QUIET, or "?" buttons are pressed. If the DISPENSE or QUIET buttons are pressed (steps 2040, 2050) then a message will be displayed on the LCD display indicating that it is not the appropriate time for medication to be taken (step 2060). The display then informs the patient (step 2070) when the last medications were taken, when the next medications are scheduled to be taken, of any medications which were missed, and records for the report that the button was pressed. The main routine then continues at step 2090.

If the "?" button is pressed (step 2080), then the display informs the patient (step 2070) when the last medications were taken when the next medications are scheduled to be taken, of any medications which were missed, and records for the report that the button was pressed. The main routine then continues at step 2090.

As shown in FIG. 14B the main routine then determines in sequence 1) whether the pill cartridge has accidentally moved (step 3000) responsive to the output of the index LED/receiver pair; 2) whether the overdose protection drawer is closed (step 3020); 3) whether the battery power is below an acceptable threshold (step 3040); 4) whether it is time to replace the pill cartridge (step 3060); 5) whether it is time for a report to be transmitted to the caregiver (step 3080); 6) whether the program switch is set (step 3100) to enable the programming of the dispenser as detailed in FIG. 13 step 1000.

If the cartridge has moved not under the direction of the controller (step 3000), then the cartridge subroutine (step 3010) is executed. The cartridge subroutine returns to the main routine at step 3020. As shown in FIG. 14B, if the overdosage protection drawer is open (step 3020), then the system failure subroutine (step 3030) is executed. The system failure subroutine ultimately returns to the main routine from step 3110. If the battery power is low, then the battery-low subroutine (step 3040) is executed. The battery-low subroutine may return to the main routine at step 3060, or may proceed to the system failure subroutine.

The next decision in the main routine is whether the current time is greater than or equal to the cartridge removal time (step 3060). If so then the replace cartridge subroutine (step 3070) is executed. The replace cartridge subroutine may either return to the main routine at step 3080, or may proceed to the system failure subroutine.

If the present time is greater than or equal to the time to report the dispenser status to the caregiver, then the report subroutine (step 3090) is executed. The report subroutine returns to the main routine at step 3100.

The final decision in the main routine is whether the program switch has been set (step 3100). This switch maybe set by a software flag when the cartridge is removed as part of the replace cartridge subroutine or by plugging the remote programming device into the pill dispenser programming port. If it is set then the programming subroutine, as shown in FIG. 13 step 1000, is executed. The programming subroutine returns to the main routine at step 3110. The main routine then repeats itself as shown in FIGS. 14A and 14B.

Figure 14C:
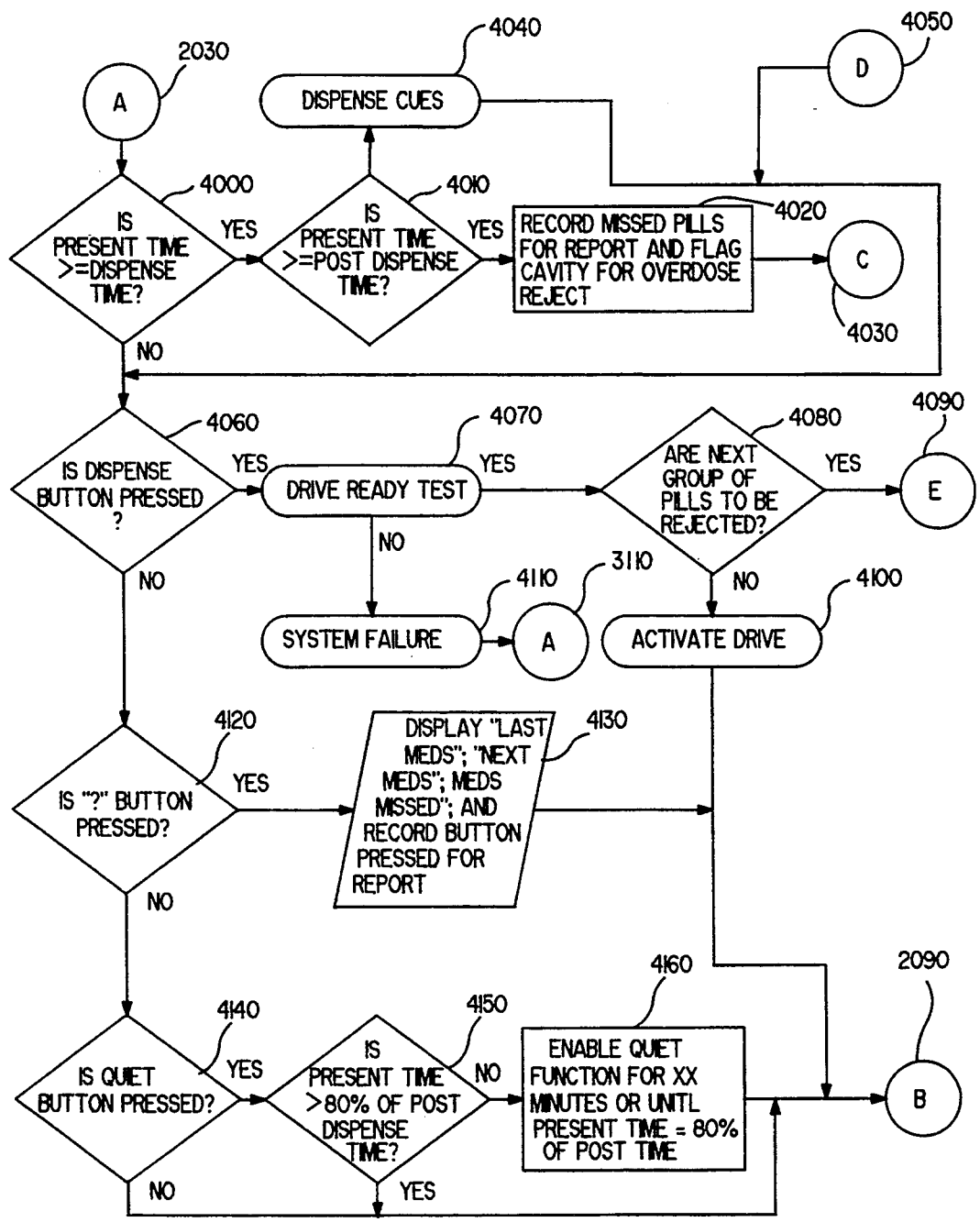

The pill dispense subroutine, which is shown in FIG. 14C, begins by deciding whether the present time is greater than or equal to the dispense time (step 4000). If so, then the pill dispense routine decides whether the present time is less than the post dispense time (step 4010). If not, the fact that the pills that were to be dispensed in this window of time were missed, is recorded (step 4020) for latter reporting and subsequent diversion of these pills to the overdose compartment. The pill dispense routine returns to the main routine from step 4030.

If the present time is less than the post dispense time (step 4010), then the dispense cues subroutine (step 4040) is executed. This subroutine will return to the pill dispense subroutine at step 4060.

If the present time is not greater than or equal to the dispense time (step 4000), then the pill dispense routine proceeds to step 4060 and queries whether the DISPENSE button is pressed. If not then the program proceeds to step 4120. If it is pressed, then the drive ready test subroutine is executed (step 4070) and the subroutine determines whether the drive is ready. If not, the system failure subroutine is executed (step 4110), and returns to the main routine at step 3110. Otherwise the program determines whether or not the next group of pills is to be deposited in the overdose protection drawer (step 4080). If so the overdose protection subroutine is executed (step 4090). The overdose protection subroutine returns to the pill dispense routine at step 4050, or to the main routine (step 3110) if a system failure occurs during execution of the overdose protection subroutine.

If the pills are not to be deposited in the overdose protection drawer, then the pill dispense subroutine then proceeds to dispense the pills by executing the activate drive subroutine (step 4100). The program then returns to the main routine at step 2090.

Step 4120 queries whether the "?" button is pressed. If so, information is displayed and recorded (step 4130). The pill dispense subroutine then returns to the main routine at step 2090.

If the "?" button is not pressed, then the pill dispense routine proceeds to step 4140 and queries whether the QUIET button is pressed. If so it determines whether the present time is greater then 80% of the post dispense time in step 4150. If not the quiet function, which disables the tone from sounding, is executed (step 4160) for several minutes, for example 15 minutes, or until the present time is greater then 80% of the post dispense time, which ever comes first. The pill dispense subroutine then returns to the main routine at step 2090. If the QUIET button is not pressed, then the pill dispense subroutine returns to the main routine at step 2090.

Figure 14D:
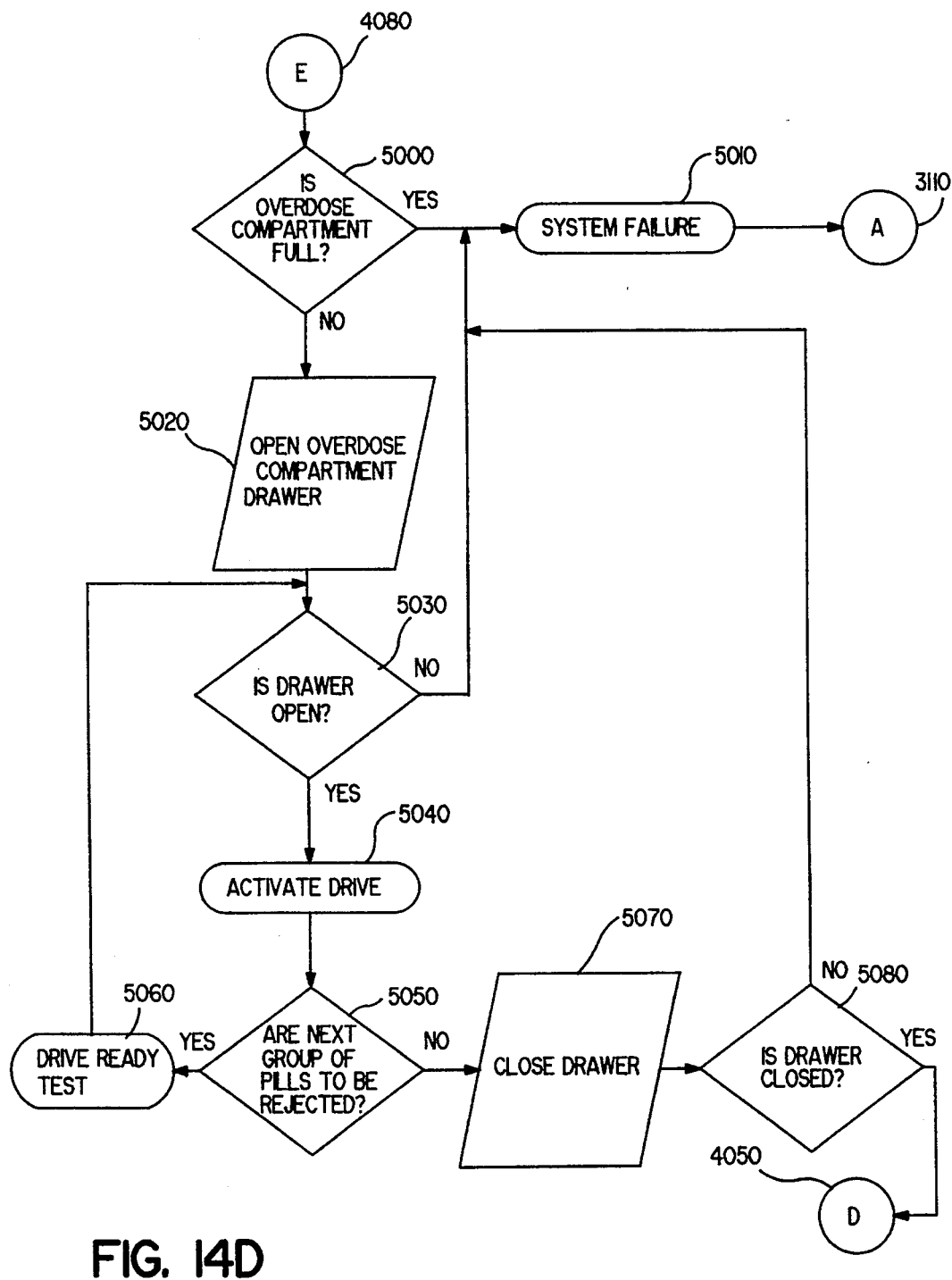

The overdose protection subroutine, beginning at step 4090 of FIG. 14D, determines whether the overdose protection area is full by counting the number of times the subroutine was previously called. If it is full the system failure subroutine is executed (step 5010) and the program returns to the main routine at step 3110. If it is not full the drawer is opened by energizing a solenoid (step 5020). If after a short period of time the drawer is still sensed as not open (step 5030), then the system failure subroutine is executed (step 5010). If the drawer is sensed as open, then the activate drive subroutine is executed (step 5040). When this subroutine is successfully executed, the pills are dropped into the overdose protection drawer. The overdose protection subroutine decides whether the next cavity of pills must also be diverted (step 5050). If so then the overdose protection subroutine is repeated at step 5030. If the next cavity is to be dispensed then the drawer is closed by deenergizing the solenoid (step 5070). If after a short period of time, the drawer is not sensed as closed the system failure subroutine is executed (step 5010). If the drawer is sensed as closed, then this subroutine is completed and the program returns at step 4050 to the pill dispense subroutine (FIG. 14C).

The system failure subroutine first decides whether a local report is required. If so several loud pulsing tones will be sounded to draw the patient's attention to the dispenser. The display informs the patient that the pill dispenser has failed to operate properly, which part has malfunctioned, and how to get help. If a local report is not required, or when it is complete, then a remote report is made to the caregiver. All other functions of the dispenser are disabled.

The drive ready test subroutine first turns off the index complete LED, and if the sensor recognizes this change in state, then the test is passed and the dispenser is ready to turn on the motor and move the drive wheel. If the system does not recognize the change in state, then the system failure subroutine is executed.

The activate drive subroutine first turns on the index complete LED and the drive motor. The drive wheel rotates peeling the cover from the cartridge and rotating the cartridge. As the cartridge is rotated the light from the index complete LED is blocked from the index complete sensor by the cartridge. As this motion continues, the uncovered cavity drops its pills through the passage and eventually the index complete sensor sees the light from its associated LED and the motor is stopped.

The dispense cues subroutine (step 4040) flashes the dispense light on and off and displays the messages on the LCD display instructing the patient to press the dispense button and to take their medication. If the quiet function has not been activated by the execution of the quiet subroutine, the pulsing tone is turned on and off on a half second duty cycle for several seconds. The tone is then turned off for several more seconds, for example as much as 60 seconds. If the dispense button is not pressed, then the pulsing tone is repeated at a higher volume. This cycle is repeated for several minutes. After several repetitions the time of silence between the cycle of pulsing tones is increased to 5 minutes. If the dispense button is pressed at any time during this subroutine, then the subroutine is completed. If the dispense button is not pressed during this subroutine, then when the present time equals the post dispense time the subroutine is complete and returns to the pill dispense subroutine at step 4060.

The cartridge position subroutine (step 3010) tests the index complete LED/sensor pair. If the cartridge is being moved by the activate drive subroutine, then the cartridge position subroutine returns to the main program at step 3020. Otherwise, if the sensor senses light from the LED, then the test is passed and the subroutine returns to the main routine. If the sensor does not sense light from the LED, then a message is displayed explaining that the cartridge has moved and should be checked and adjusted, or that the LED/sensor pair has malfunctioned. This condition is recorded for later reporting and the dispense function is disabled from operating. The subroutine then returns to the main routine at step 3020.

The low battery subroutine (step 3050) tests the battery voltage level. If the voltage level is high enough for reliable operation, then the subroutine returns to the main routine. If the voltage is too low for reliable operation of the pill dispenser, then the system failure subroutine is executed. If the battery is low, but can still be operated reliably, then instructions are displayed telling the patient that the battery is low, it should be replaced, and how to replace it or where to call for help in replacing it. This low battery condition is recorded for later reporting. The subroutine returns to the main routine at step 3060.

The replace cartridge subroutine (step 3070) first tests the cartridge removal complete LED/sensor pair by turning the LED on. If it is sensed as dark, the system failure subroutine will be executed. If it is sensed as illuminated, the test is passed and a solenoid is activated to open the nip between the drive wheel and the partition, to allow removal of the cartridge and its attached cover. The instruction to remove the cartridge is displayed. As the cartridge is removed the cartridge removal complete sensor will first sense dark. When it senses light again, the cartridge insertion complete and index complete LED/sensor pairs are tested. The LEDs are turned on, if either sensor senses dark, then the system failure subroutine is executed. If both are sensed as illuminated then the test is passed and the instruction to insert a new cartridge is displayed. When the cartridge insertion complete sensor senses dark, then the solenoid is deenergized, which closes the partition and forms a nip with the drive wheel griping the cartridge cover. The drive wheel is then turned. If after 3 seconds the index complete sensor has not sensed light, then the drive is stopped and the display instructs the patient to visually check for proper engagement of the cover in the nip. After a few seconds the solenoid will energize and reopen the nip to allow for adjustment of the cartridge cover. The display will instruct the patient to press the "?" button when the adjustment is complete. The solenoid will deenergize and the nip will then close again and the drive wheel will turn. If after 3 seconds the index complete sensor has not sensed light the system failure subroutine is executed. If the index complete sensor does sense light, then the drive wheel is stopped and the display informs the patient that the new cartridge is inserted properly and the dispenser is ready for use. The subroutine returns to the main routine at step 3080.

The remote report subroutine (step 3090) first decides if the home phone is busy. If it is busy, after a delay of 5 minutes the home phone is checked again to decide if it is still busy. This procedure is repeated until the home phone is not busy. When the home phone is not busy then the pill dispenser automatically dials the caregiver's phone number. If the line is busy, after a 5 minute delay the number is redialed again. This procedure is continued until the caregiver's phone is no longer busy. When the connection is made between the home phone and the caregiver's phone then the report data is transmitted. After the transmission is complete the phones are disconnected. The subroutine returns to the main routine at step 3100.

Those skilled in the art will appreciate that the invention may be embodied in a variety of devices beyond those described above and numerous modifications thereto may be made without departing from the scope of the invention.

I claim:

1. A medication dispensing device for providing medication doses within selected periods of time, said device comprising:
   housing means defining a first and second opening;
   medication containment means including a plurality of individually sealed medication dosage storage areas for containing medication doses, received within said first opening in said housing, wherein each said storage area has an associated time period during which said dosages may be dispensed;
   first signal generating means for generating a request signal;
   dispensing means for causing medication doses that are requested within their respective time periods to be dispensed from said device through said second opening;
   medication collection means for preventing medication doses that are not requested within their respective time periods from being dispensed from said device;
   control means for controlling said dispensing means, said medication collection means, responsive to said request signal and said time periods.

2. A medication dispensing device as claimed in claim 1, wherein said medication containment means further includes a flexible seal, and said dispensing means includes a wheel engageable with said seal to remove said seal as said wheel is rotated.

3. A medication dispensing device as claimed in claim 1, wherein device further includes display means for displaying information regarding the times associated with each cavity.

4. A medication dispensing device as claimed in claim 1, wherein each of said compartments is sealed from moisture and airborne particles.

5. A medication dispensing device as claimed in claim 1, wherein said device is portable.

6. A medication dispensing device as claimed in claim 1, wherein said device further includes a liquid crystal display for displaying information responsive to said controller.

7. A medication dispensing device as claimed in claim 1, wherein said device further includes report means for generating a report.

8. A medication dispensing device as claimed in claim 1, wherein said device further includes a port for communicating to a programming unit.

9. A medication dispensing device as claimed in claim 1, wherein said device further includes a modem unit and a telephone port for communicating through telephone lines.

* * * * *